United States Patent
Nakamura

(10) Patent No.: US 7,495,754 B2
(45) Date of Patent: Feb. 24, 2009

(54) DIFFERENTIAL REFRACTOMETER AND ITS ADJUSTING METHOD

(75) Inventor: Takafumi Nakamura, Kyoto (JP)

(73) Assignee: Shimadzu Corporation, Kyoto-shi (JP)

( * ) Notice: Subject to any disclaimer, the term of this patent is extended or adjusted under 35 U.S.C. 154(b) by 317 days.

(21) Appl. No.: 11/532,935

(22) Filed: Sep. 19, 2006

(65) Prior Publication Data
US 2007/0076192 A1   Apr. 5, 2007

(30) Foreign Application Priority Data
Sep. 30, 2005   (JP) .............................. 2005-285710

(51) Int. Cl.
*G01N 21/41* (2006.01)

(52) U.S. Cl. ..................................................... 356/130

(58) Field of Classification Search .................. 356/130
See application file for complete search history.

(56) References Cited

U.S. PATENT DOCUMENTS
5,398,110 A   3/1995   Kitaoka

FOREIGN PATENT DOCUMENTS
JP   60250230 A   * 12/1985
JP   61-226640   10/1986

* cited by examiner

*Primary Examiner*—Gregory J Toatley, Jr.
*Assistant Examiner*—Amanda H Merlino
(74) *Attorney, Agent, or Firm*—Rankin, Hill & Clark LLP

(57) ABSTRACT

Adjustment of a differential refractometer includes the steps of (a) equally focusing a slit image on separate portions of a photodetector, (b) decreasing the quantity of light of measuring beam, (c) making parallel movement of the slit image on the photodetector by a predetermined displacement, and (d) increasing the quantity of light of the measuring beam.

2 Claims, 2 Drawing Sheets

DIFFERENTIAL REFRACTOMETER AND ITS ADJUSTING METHOD

TECHNICAL FIELD

This invention relates to a differential refractometer which is employed as a detector in an analyzing device such as a liquid chromatograph, and its adjusting method.

RELATED ART

The differential refractometer includes a flow cell having two cells divided by a partition wall inclined with respect to an optical axis of a measuring beam, a photodetector for receiving the measuring beam refracted by the flow cell, and an optical system for applying the measuring beam through a slit to the flow cell, guiding the measuring beam from the flow cell to the photodetector and focusing the measuring beam as a slit image on the photodetector. In the flow cell, a sample solution is passed through one of the two cells and a reference solution is passed through the other of the two cells. On the basis of a quantity of displacement of the slit image on the photodetector, the differential refractometer detects a change of the refractive index of the sample solution.

FIG. 3 schematically illustrates an example of the differential refractometer. Light emitted from a light source 8 passes through a slit 10 to constitute a measuring beam 12. The measuring beam 12 is applied onto a flow cell 16 through a lens 14 located in front of the flow cell 16. The flow cell 16 is composed of two cells 20a and 20b divided by a partition wall 18. The cell 20a has an inlet port 22i and an outlet port 22o, and the cell 20b has an inlet port 24i and an outlet port 24o. Behind the flow cell 16, a mirror 26 is located. The measuring beam having passed through the flow cell 16 is reflected by the mirror 26 and passes through the flow cell 16 again. The reflected light from the mirror 26, having passed through the flow cell 16, is focused as a slit image on a photodetector 30 by the lens 14. In order to make the parallel movement of the slit image on the photodetector 30, a zero glass 28 is arranged on the optical axis of the measuring beam. By operating the zero glass 28 using a pulse motor 32 driven by a motor driving circuit 34, the parallel movement of the slit image on the photodetector 30 can be made. Reference numeral 36 denotes a signal processing circuit which executes signal processing for acquiring a change in the refractive index of the sample solution on the basis of a signal which is produced and output from the photodetector 30.

In a related-art differential refractometer, as shown in FIG. 4A, the photodetector divided into two portions 2-1 and 2-2 by a straight line 4 perpendicular to a movement direction (X direction) of the slit image 6 has been employed, and a displacement of the slit image 6 on the photodetector is detected. Assuming that the slit image moves toward e.g. the element portion 2-2 if the refractive index of the sample solution increases, the signal processing circuit computes $S = C \cdot (s2 - s1)/(s2 + s1)$ to be outputted. Now, s1 and s2 represent detected outputs from the portions 2-1 and 2-2 of the photodetector, respectively. C represents a certain constant. The output of the signal processing circuit changes according to the quantity of change in the refractive index of the sample solution. On the photodetector, if the entire slit image 6 enters the portion on the one side of the photodetector as shown in FIG. 4B, the signal produced in the photodetector will be saturated. For this reason, adjustment (balancing) operation of the slit image is made so that at the time of measurement initiation, the slit image 6 is centrally located so as to straddle the straight line 4 for separation as shown in FIG. 4A.

An application example of the analyzing device in which the theory of differential refraction is employed as a detector is a liquid chromatograph. The liquid chromatograph has two purposes of analysis and preparative use. In the case of the purpose of preparative use, the sample with a relatively higher density is caused to flow. Therefore, if the differential refractometer with high sensitivity for analysis is used for the preparative use, the signal produced in the photodetector will be saturated. Thus, there has been proposed a differential refractometer having the photodetector divided into four portions so that both uses of high sensitivity and low sensitivity for analysis and preparative use can be dealt with by the photodetector and the subsequent signal processing circuit even if the flow cell is not replaced in the differential refractometer (Patent Reference 1: U.S. Pat. No. 5,398,110).

As an item for evaluating the performance of the photodetector, there is a signal-to-noise ratio (S/N). In order to improve the S/N, a larger quantity of light incident on the photodetector is desired. However, if the quantity of light is excessively increased, a circuit which reads the signal output from the photodetector will be saturated. In order to avoid such inconvenience, the differential refractometer is adjusted appropriately in its the quantity of incident light. Industrially, on the basis of the "appropriate quantity of light" determined uniquely, the differential refractometer is adjusted. However, the differential refractometer has minute variations in the distance from the flow cell to the photodetector, slit width, slit position according to a combination of the constituent components. So, the "appropriate quantity of light" set uniquely during manufacture is not necessarily a real appropriate quantity of light. If the appropriate quantity of light set uniquely is less than the "real appropriate quantity of light", the S/N of the signal from the photodetector is deteriorated. Inversely, if the former is more than the latter, a measurable maximum value is decreased, thereby narrowing the measurement range. In short, the differential refractometer adjusted on the basis of the "appropriate quantity of light" set uniquely cannot exhibit the best performance in a combination of constituent components.

SUMMARY

Embodiments of the present invention provide a differential refractometer and its adjusting method.

As a result of diligent research by inventors of this invention, a method of adjustment for permitting the differential refractometer to exhibit the best performance has been found. Specifically, according to a first aspect of one or more embodiments of the invention, there is provided with a method for adjusting a differential refractometer in which a measuring beam having passed a slit is passed through a flow cell having two cells divided by a partition wall inclined with respect to an optical axis of the measuring beam so that a sample solution is passed through one of the cells and a reference solution is passed through the other of the cells, the measuring beam passed through is reflected by a mirror and passed through the flow cell again, and the measuring beam is focused as a slit image so as to extend over separate portions of a photodetector, thereby detecting a displacement of the slit image, the method comprising the steps of:

(a) equally focusing the slit image on the separate portions of the photodetector;

(b) decreasing the quantity of light of measuring beam;

(c) making parallel movement of the slit image on the photodetector by a predetermined displacement; and (d) increasing the quantity of light of the measuring beam.

Further, according to a second aspect of one or more embodiments of the invention, there is provided with a differential refractometer comprising:

a light source;

a flow cell having two cells divided by a partition wall inclined with respect to an optical axis of a measuring beam emitted from the light source so that a sample solution is passed through one of the two cells and a reference solution is passed through the other of the two cells;

a photodetector for receiving the measuring beam refracted by the flow cell, the photodetector being divided into a pair of separate portions; and an optical system for applying the measuring beam to the flow cell through a slit, guiding the measuring beam from the flow cell to the photodetector through a zero glass and focusing a slit image on the photodetector, so that the differential refractometer detects a change of a refractive index of the sample solution on the basis of outputs from the pair of separate portions of the photodetector;

a light quantity adjusting unit for increasing or decreasing the quantity of light of the measuring beam; and a control unit for controlling the optical system and the light quantity adjusting unit to executes operation of (a) equally focusing the slit image on the separate portions of the photodetector, (b) decreasing the quantity of light of the measuring beam, (c) making a parallel movement of the slit image on the photodetector by a predetermined displacement, and (d) increasing the quantity of light of the measuring beam.

In accordance with this adjusting method, the maximum value of the input value of a circuit which reads the signal output from the photodetector can be set within a range capable of measuring the displacement. In accordance with this configuration, an operator can appropriately execute the adjustment operation.

Various implementations may include one or more the following advantages. For example, the refractive index of the sample solution can be detected with high S/N while keeping a measurable range. Since the "real appropriate quantity of light" is set in a state assembled by combining the constituent components of the differential refractometer, the differential refractometer can exhibit the best performance without deteriorating its performance.

DETAILED DESCRIPTION

Figure 1:
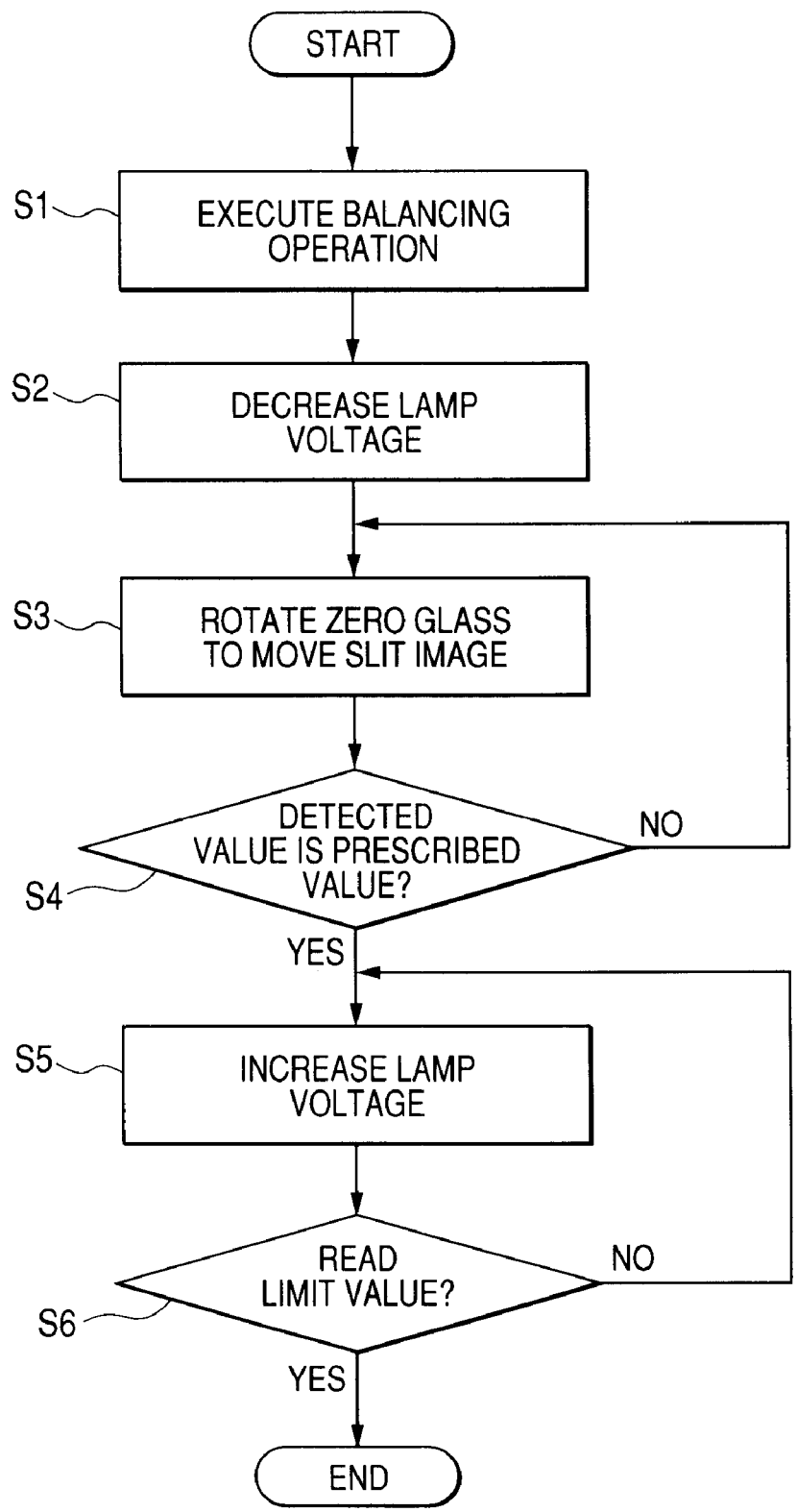
FIG. 1 is a flowchart showing the procedure of adjusting a differential refractometer according to this invention.

Now referring to FIG. 1, an adjusting operation according to this invention will be explained. As a preparation at the time of adjustment, the interior of two cells (the sides of a sample solution and a reference solution) of a flow cell are filled with the same kind of liquid (mobile phase). In this state, first, the measuring beam emitted from the light source is passed through the flow cells and the optical system and focused as a slit image on the photodetector. In this case, balancing operation is made so that the slit image focused on the photodetector straddles the center line of the photodetector divided into two separate portions (S1).

Next, the quantity of light of the measuring beam emitted from the light source is decreased to ½ (S2). More specifically, the lamp voltage of the light source is decreased. The quantity of light can be decided in terms of the strength of the signal produced from the photodetector. Using the value of the signal strength, the quantity of light may be decreased to ½ as large as before it is decreased.

The zero glass is rotated to make the parallel movement of the slit image on the photodetector by a predetermined displacement (S3 to S4). The displacement due to the parallel movement can be acquired on the basis of the signal strength of the respective separate portions of the photodetector. Now, the predetermined displacement (and its unit) differs according to the specification of the type of the device, but may be set at a slightly larger than the maximum value of the displacement which can be measured by the differential refractometer. For example, if the maximum value of the displacement which the differential refractometer can measure is 500 μRIU (refractive index unit), 600 μRIU may be set as the predetermined displacement.

After the slit image has been shifted to reach the predetermined displacement, the quantity of light once decreased in S2 is increased to a predetermined value. Since the slit image deviates from the center line of the photodetector, the signal representative of the displacement increases as the quantity of light incident on the photodetector is increased. The signal processing circuit 36 includes an A/D converter. The range that the signal processing circuit can detect the signal, which is produced based on the quantity of light incident on the photodetector and output from the photodetector, depends on the input-enabling range of the A/D converter, and have a value at which the signal output from the photodetector is saturated. If the input-enabling range of the A/D converter is within −5 to 5 V, the quantity of light may be increased so that it exhibits the upper limit of 5 V (or −5 V). In order that the value outside the input-enabling range of the A/D converter is not inputted as an input value in measurement, the predetermined value may be set at 4.9 V (or −4.9 V) so as to take a margin.

After having been subjected to steps of S1 to S6, balancing operation is made so that the slit image on the photodetector straddles the center line of the photodetector divided into the two portions. Thus, the adjustment is completed.

When the measurement is initiated and then a target material flows into the cell on the side of the sample solution in the flow cell, a difference of the refractive index occurs between the liquid on the sample solution side and the liquid on the reference solution side so that the slit image focused on the photodetector is displaced. On the basis of the displacement, the photodetector produces a signal, thereby serving as the differential refractometer.

Figure 2:
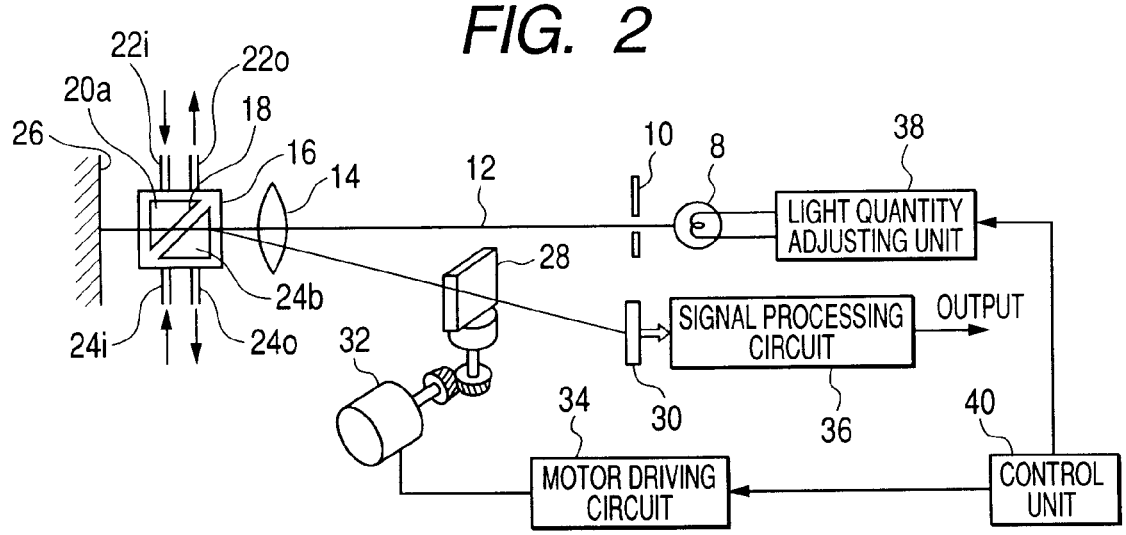
FIG. 2 is a diagram showing the configuration of the differential refractometer according to this invention.
Figure 3:
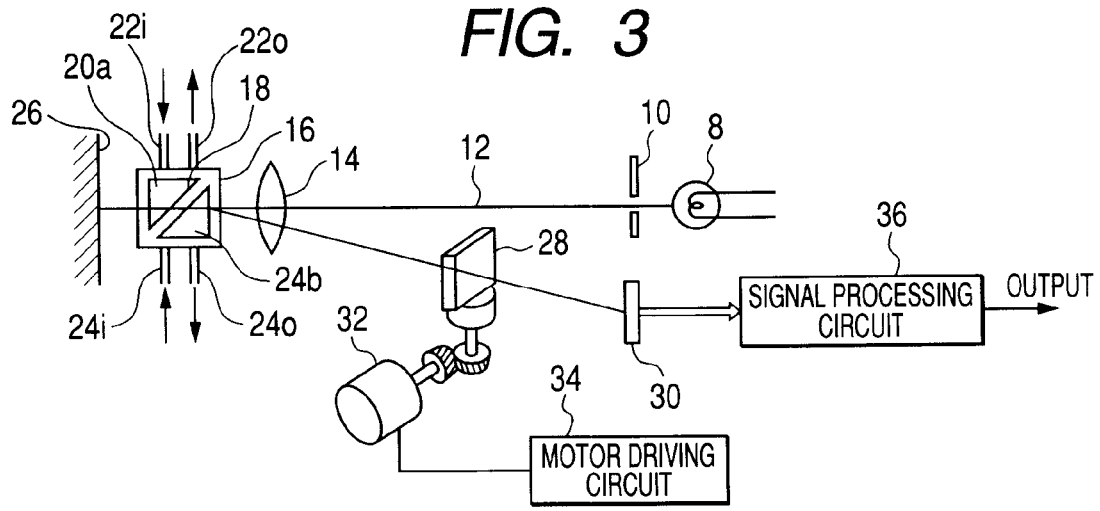
FIG. 3 is a diagram showing the configuration of a general differential refractometer.
Figure 4A:
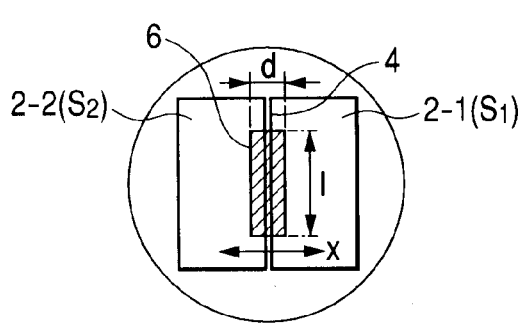
FIGS. 4A and 4B are views for explaining the theory of the general differential refractometer.
Figure 4B:
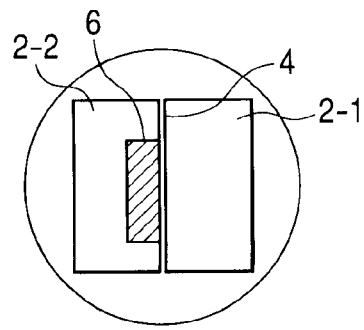

FIG. 2 is a schematic diagram of a differential refractometer according to the invention of this application. The differential refractometer includes a light quantity adjusting unit 38 for adjusting the quantity of light to be emitted from the light source 8. The light quantity adjusting unit 38 is controlled by a control unit 40. When an operator executes an adjustment requiring operation, the control unit 40 controls the light quantity adjusting unit 38 and the motor driving circuit 34 to make the adjustment as shown in FIG. 1.

The above adjustment operation is automatically executed, for example when the differential refractometer is actuated. Further, at the other time than when the differential refractometer is actuated, e.g. when measurement of the sample is not executed, and after maintenance or component replacement has been done, if the adjusting method according to this invention is carried out, the differential refractometer can set "the real appropriate quantity of light", thereby always exhibiting the best performance.

The embodiments described above are only examples of this invention. It is apparent that this invention includes appropriate changes or modifications within the spirit of the invention.

The differential refractometer according to this invention is adopted as a detector for the liquid chromatograph for analysis or preparative use.

DRAWINGS:

FIG. 1
START
S1 EXECUTE BALANCING OPERATION
S2 DECREASE LAMP VOLTAGE
S3 ROTATE ZERO GLASS TO MOVE SLIT IMAGE
S4 DETECTED VALUE IS PRESCRIBED VALUE?
S5 INCREASE LAMP VOLTAGE
S6 READ LIMIT VALUE?
END

FIG. 2
34 MOTOR DRIVING CIRCUIT
36 SIGNAL PROCESSING CIRCUIT
38 LIGHT QUANITY ADJUSTING UNIT
40 CONTROL UNIT

FIG. 3
34 MOTOR DRIVING CIRCUIT
36 SIGNAL PROCESSING CIRCUIT

What is claimed is:

1. A method for adjusting a differential refractometer in which a measuring beam having passed a slit is passed through a flow cell having two cells divided by a partition wall inclined with respect to an optical axis of the measuring beam so that a sample solution is passed through one of the cells and a reference solution is passed through the other of the cells, the measuring beam passed through is reflected by a mirror and passed through the flow cell again, and the measuring beam is focused as a slit image so as to extend over separate portions of a photodetector, thereby detecting a displacement of the slit image, the method comprising the steps of:
   (a) equally focusing the slit image on the separate portions of the photodetector;
   (b) decreasing the quantity of light of measuring beam;
   (c) making parallel movement of the slit image on the photodetector by a predetermined displacement; and
   (d) increasing the quantity of light of the measuring beam.

2. A differential refractometer comprising:
   a light source;
   a flow cell having two cells divided by a partition wall inclined with respect to an optical axis of a measuring beam emitted from the light source so that a sample solution is passed through one of the two cells and a reference solution is passed through the other of the two cells;
   a photodetector for receiving the measuring beam refracted by the flow cell, the photodetector being divided into a pair of separate portions; and
   an optical system for applying the measuring beam to the flow cell through a slit, guiding the measuring beam from the flow cell to the photodetector through a zero glass and focusing a slit image on the photodetector, so that the differential refractometer detects a change of a refractive index of the sample solution on the basis of outputs from the pair of separate portions of the photodetector;
   a light quantity adjusting unit for increasing or decreasing the quantity of light of the measuring beam; and
   a control unit for controlling the optical system and the light quantity adjusting unit to executes operation of
   (a) equally focusing the slit image on the separate portions of the photodetector,
   (b) decreasing the quantity of light of the measuring beam,
   (c) making a parallel movement of the slit image on the photodetector by a predetermined displacement, and
   (d) increasing the quantity of light of the measuring beam.

* * * * *